United States Patent [19]
Kawaguchi et al.

[11] Patent Number: 5,768,940
[45] Date of Patent: Jun. 23, 1998

[54] SAMPLE COLLECTOR

[75] Inventors: Junichiro Kawaguchi, Uenohara-machi; Akira Fujiwara, Chigasaki; Shujiro Sawai, Sagamihara; Masanao Abe, Sagamihara; Akiko Nakamura, Sagamihara, all of Japan

[73] Assignee: The Director-General of The Institute of Space and Astronautical Science, Sagamihara, Japan

[21] Appl. No.: 848,731

[22] Filed: May 22, 1997

Related U.S. Application Data

[63] Continuation-in-part of Ser. No. 673,314, Jun. 28, 1996, abandoned.

[30] Foreign Application Priority Data

Dec. 7, 1995 [JP] Japan ................................. 7-319060

[51] Int. Cl.$^6$ ............................. G01N 1/08; E21B 49/02
[52] U.S. Cl. ............................ 73/864.41; 73/864; 175/20
[58] Field of Search ................................ 73/864, 864.41, 73/864.44, 864.4, 864.31; 175/4, 20

[56] References Cited

U.S. PATENT DOCUMENTS

| | | | |
|---|---|---|---|
| 3,843,198 | 10/1974 | Reynolds | 73/864.41 X |
| 4,085,973 | 4/1978 | Payne | 73/864 X |
| 4,236,402 | 12/1980 | McGuire | 73/864.41 X |
| 4,437,333 | 3/1984 | Honds | 73/863.23 X |
| 4,594,885 | 6/1986 | Rodger | 73/864.45 X |
| 4,665,791 | 5/1987 | Bugiel | 175/4 X |
| 4,754,655 | 7/1988 | Parker, III et al. | 73/864.44 |
| 4,802,143 | 1/1989 | Smith | 73/152.28 X |
| 4,869,115 | 9/1989 | Edwards et al. | 73/864.41 X |
| 4,887,413 | 12/1989 | Tucker, Jr. | 73/864.44 X |
| 4,991,452 | 2/1991 | Dillard et al. | 73/864.44 |

OTHER PUBLICATIONS

*Patent Abstracts of Europe* EP 00469427A1 Feb. 5, 1992 "Sampling Device".

*Primary Examiner*—Thomas P. Noland
*Attorney, Agent, or Firm*—Oblon, Spivak, McClelland, Maier & Neustadt, P.C.

[57] ABSTRACT

A sample collector of this invention includes a projectile projecting unit in which a projectile is loaded and which has a projecting outlet for projecting out the projectile loaded therein, an enclosed container which is communicated with the projecting outlet of the projectile projecting unit, which has a projectile passing hole arranged at a position located away from the projecting outlet, the passing hole allowing the projectile to pass through it after the projectile is projected out from the projecting outlet, and which covers a space between the projecting outlet of the projectile projecting unit, and a kinetic energy absorbing mechanism which is arranged around a projectile path between the projecting outlet of the projectile projecting unit and the projectile passing hole of the enclosed container. The kinetic energy absorbing mechanism may be an independent active type such as brushes or an integral passive type structured by a part of the container.

11 Claims, 2 Drawing Sheets

SAMPLE COLLECTOR

CROSS-REFERENCE TO RELATED APPLICATIONS

This is a continuation-in-part application of U.S. patent application Ser. No. 08/673,314 filed Jun. 28, 1996 and now abandoned.

BACKGROUND OF THE INVENTION

This invention relates to a sample collector which is used with it being attached to a supporting base.

It is well known that such kind of sample collector described above is used with it being attached to a supporting base, such as an interplanetary spacecraft.

As the conventional sample collectors, the following two kinds of sample collectors have been known.

The first kind of sample collector projects a projectile from the interplanetary spacecraft to stick it into a surface of a celestial body as an object from which a sample is to be collected. A sample storing means is provided in the projectile to store a sample obtained from a portion of the surface of the celestial body in which the projectile is sticked. The interplanetary spacecraft collects the projectile after it projects the projectile, so that the sample of the surface of the celestial body contained in the projectile, is collected in the spacecraft.

The second kind of sample collector projects a projectile from the interplanetary spacecraft to break a surface of a celestial body. And, fragments (that is, samples) of the surface of the celestial body are collected by sample collecting means which is independent of the projectile and is provided on the spacecraft.

BRIEF SUMMARY OF THE INVENTION

The conventional first kind of sample collector, however, can not collect the sample of the celestial body when the projectile fails to stick into the surface of the celestial body, and needs protecting means for protecting the sample collector and the spacecraft against fragments (that is, samples) of the surface of the celestial body which are formed by striking of the projectile against the surface of the celestial body and are ejected therefrom, and against the projectile which is projected into the surface of the celestial body but can not be sticked into the surface. Such protection is very important on a celestial body on which gravity is small.

The conventional second kind of sample collector, as the same as the conventional first kind of sample collector, also needs protecting means for protecting the sample collector and the spacecraft against fragments (that is, samples) of the surface of the celestial body which are formed by striking of the projectile against the surface of the celestial body and are ejected therefrom, and against the projectile which is projected on the surface of the celestial body but can not be sticked into the surface to be rebounded therefrom. Further, in the conventional second kind of sample collector, a structure of the independent sample collecting means becomes necessarily complex in order to collect the fragments of the surface of the celestial body which may be scattered on the surface of the celestial body, and a sample collecting efficiency of the sample collecting means is low. And, the scattering range of the fragments on the surface of the celestial body becomes large to lower the sample collecting efficiency while the gravity of the celestial body becomes low.

This invention is derived from the above described circumstances, and an object of this invention is to provide a sample collector which can collect a sample with a good sample collecting efficiency even if a projectile fails to stick into a surface of an object from which the sample is to be collected, and can exactly prevent fragments (that is, samples) of the surface of the object which are formed by striking of the projectile against the surface of the object and are ejected therefrom, and the projectile which is projected on the surface of the object but can not be sticked into the surface to be rebounded therefrom, from striking on the sample collector or a supporting base on which the sample collector is attached and from breaking the sample collector or the supporting base, so that the fragments or the projectile does not damage the sample collector or the supporting base.

In order to achieve the above described object of this invention, a sample collector according to this invention which is used with it being attached to a supporting base, comprises a projectile projecting unit in which a projectile is loaded and which has a projecting outlet for projecting out the projectile loaded therein; an enclosed container which is communicated with the projecting outlet of the projectile projecting unit, which has a projectile passing hole arranged at a position located away from the projecting outlet and located adjacently to an object from which a sample is to be collected, the passing hole allowing the projectile to pass through it after the projectile is projected out from the projecting outlet, and which covers a space between the projecting outlet of the projectile projecting unit and the projectile passing hole to provide a sample collecting room; and kinetic energy absorbing means which is arranged around a projectile path between the projecting outlet of the projectile projecting unit and the projectile passing hole of the enclosed container. When the sample collector according to this invention and structured as described above is used to collect samples from an object from which the samples are to be collected, at first the projectile projecting unit projects the projectile from the projecting outlet thereof and the projectile passing hole of the enclosed container to strike the projectile against the surface of the object. Almost all of fragments (that is, samples) of the object which are formed by striking of the projectile against the surface of the object can be collected through the projectile passing hole of the enclosed container into the sample collecting room of the enclosed container. Further, since the kinetic energy absorbing means absorbs the kinetic energy of the fragments, the fragments collected through the projectile passing hole of the enclosed container into the sample collecting room therein do not damage the enclosed container, and the fragments are not rebounded from the inner surface not to escape out from the projectile passing hole of the enclosed container. By locating the projectile passing hole of the enclosed container adjacently to the object as nearly as possible, or by preferably contacting the projectile passing hole onto the object, the fragments of the sample can not be scattered out of the sample collecting room of the enclosed container, thus, the fragments can not strike the sample collector or the supporting base to damage it. This makes the collecting efficiency of the sample become high.

In the sample collector according to this invention and structured as described above, the supporting base may be an interplanetary spacecraft. Of course, the supporting base may be various kinds of transporters, such as, for example an airplane which can stop in the air like a helicopter, an automobile, a ship, and any carrier equipped with moving means like wheels, other than the interplanetary spacecraft. Alternately, the supporting base according to this invention may be carried by a person or persons.

Further, in the sample collector according to this invention and structured as described above, the kinetic energy absorbing means may be an active type or a passive type. A brush as one example may be included in the active type kinetic energy absorbing means because the brush is independent of the container and actively structures the kinetic energy absorbing means. Since the brush is simple in its structure, is performed almost without trouble, and is light in weight, the brush is particularly preferable as the kinetic energy absorbing means when the supporting base is the interplanetary spacecraft.

The active type kinetic energy absorbing means may have a bag-like shape or a net-like shape other than the brush. The bag-like or net-like kinetic energy absorbing means may be loosely deformed when the sample flied out from the object strikes it, and absorbs the kinetic energy of the sample.

The kinetic energy absorbing means may be preferably arranged in the enclosed container such that a distance from it to the projectile projecting outlet is larger than that from it to the projectile passing hole. Such arrangement makes a possibility that the sample jumps out to the outside of the enclosed container through the projectile passing hole, more lower.

More further, in the sample collector according to this invention and structured as described above, the sample collector may further comprises enclosed container approaching and separating means which connects the supporting base and the enclosed container with each other, and which selectively approaches or separates the projectile passing hole of the enclosed container to or from an object from which an sample is to be collected, and it is preferable that the enclosed container approaching and separating means has a rigid structure. The approaching and separating means more increase the collecting efficiency of the sample.

The enclosed container approaching and separating means may have a bendable structure such a wire. In this case, the enclosed container is suspended from the supporting base through the wire, and is approached to the object located under the supporting base and is separated therefrom. However, if a total of the mass of the projectile projecting unit and that of the enclosed container is smaller than a reaction applied on the projectile projecting unit when the projectile is projected from the projecting unit, the enclosed container, together with the projecting unit, is jumped off from the object by the reaction so that almost all of the fragments (that is, samples) of the object may not be collected into the sample collecting room of the enclosed container through the projectile passing hole.

Such disadvantage described above can be disappeared by structuring the enclosed container approaching and separating means with a rigid structure such as a telescopic pipe or a multi-articulated type leg member.

Further, in the sample collector according to this invention and structured as described above, the enclosed container may includes a sample guide member which extends from the projectile passing hole of the enclosed container to make the extending end of the sample guide member contact an object from which a sample is to be collected, the sample guide member enclosing a projectile path between the projectile passing hole of the container and the object, and guiding the sample separated from the abject when the projectile collides against the object, toward the projectile passing hole of the container.

The sample guide member more increases the collecting efficiency of the sample.

When the sample collector of this invention includes the sample guide member, the passive type kinetic energy absorbing means may be structured by the container. In this case, at least a part of an inner wall of the container, with which the sample introduced into the container by the sample guide member collides, is structured to provide multiple collision with the sample thereby absorbing the kinetic energy of the sample.

When the sample collector of this invention includes the sample guide member, the kinetic energy absorbing means may be provided the container. In this case, the kinetic energy absorbing means may be prepared independently of the container, and may have a brush, a bag-like shape, or a net-like shape.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawing, which is incorporated in and constitutes a part of the specification, illustrates preferred embodiments of the invention and, together with the general description given above and the detailed description of the preferred embodiments given below, serves to explain the principles of the invention.

DETAILED DESCRIPTION OF THE INVENTION

Figure 1:
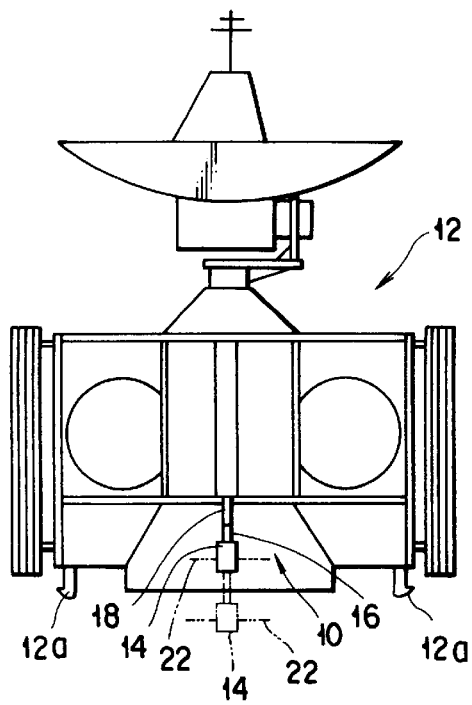
FIG. 1 is a front view schematically showing an interplanetary spacecraft which is used as one embodiment of a supporting base and is provided with a sample collector according to one embodiment of the invention.

FIG. 1 schematically shows a front view of an interplanetary spacecraft 12. This interplanetary spacecraft 12 is used as one embodiment of a supporting base and is provided with a sample collector 10 according to one embodiment of the invention. The sample collector 10 is attached to a position of a housing of the interplanetary spacecraft 12, the position being located above a lower end of a landing gear 12a of the spacecraft 12.

The sample collector 10 is generally structured by an enclosed container 14 for collecting fragments (that is, samples) of a surface of a celestial body as an object from which samples are to be collected, a projectile projection unit 16 connected to the enclosed container 14, for forming fragments from the surface of the celestial body, and enclosed container approaching and separating means 18 having upper and lower ends, the upper end being connected to the above described position of the housing of the spacecraft 12 and the lower end being connected to one of the enclosed container 14 and the projectile projection unit 16.

In a case that the interplanetary spacecraft 12 is returned to the earth, the sample collector 10 can be held in the housing of the spacecraft 12 in order to prevent heat produced by a friction between the spacecraft 12 and the atmosphere around the earth, from damaging the sample collector 10 and from influencing the sample.

In a case that an atmospheric re-entry capsule is detachably connected to the interplanetary spacecraft 12 and only the atmospheric re-entry capsule is returned to the earth, at least the sample collected in the enclosed container 14 of the sample collector 10 is transferred from the sample collecting room of the enclosed container 14 into the atmospheric re-entry capsule by a suitable well known transferring means. Of course, the enclosed container 14 in which the samples have been collected may be transferred into the atmospheric re-entry capsule.

Further, in a case that the interplanetary spacecraft 12 departs from a space mother ship toward the celestial body and returns from the celestial body to the space mother ship after the sample collector 10 attached to the spacecraft 12 collects the samples of the surface of the celestial body, the sample collector 10 may be detachably connected to the housing of the interplanetary spacecraft 12 and may be housed in the space mother ship when the spacecraft 12 returns to the space mother ship.

The enclosed container approaching and separating means 18 is reduced in its overall size to the minimum as shown by a solid line in FIG. 1, when the interplanetary spacecraft 12 is launched from the earth and is flying. The enclosed container approaching and separating means 18 is selectively extended downward from its minimum size shown by the solid line in FIG. 1 beyond the lower end of the landing gear 12a of the spacecraft 12 as shown by a two-dots chain line in FIG. 1, by a remote control after the spacecraft 12 is landed on the surface of the aimed celestial body. Of course, the enclosed container approaching and separating means 18 can be transformed from its extended condition to its minimum size, if necessary.

In this embodiment, the enclosed container approaching and separating means 18 has a telescopic structure, and can be selectively extended from its minimum size to its extended condition or retracted from the extended condition to its minimum size by means of electric power, hydraulic power, or pressurized gas power.

Next, the structure of the sample collector 10 will be described in detail with reference to FIGS. 2 and 3.

A projectile 16a is loaded in the projectile projecting unit 16, and the projectile projecting unit 16 has a projecting opening 16b through which the projectile 16a is projected out from the projecting unit 16. The projecting unit 16 moves a runner not shown by, for example a pressurized gas power or a high temperature gas pressure generated from high temperature gas generating means like an explosive, and strikes the runner against the projectile 16a so that the projectile 16a is projected out from the projecting unit 16. The runner seals the projecting opening 16b not to leak the gas from the projecting unit 16 into the enclosed container 14, and the projecting unit 16 has another gas leak hole not shown to intentionally leak the gas from the projecting unit 16 to the outer space of the sample collector 10. Since the gas is so leaked out from the projecting unit 16, the samples to be collected into the sample collector 10 are not contaminated with the gas.

The enclosed container 14 is communicated with the projecting opening 16b of the projectile projecting unit 16, has a projectile passing hole 14a which is located away from the projecting opening 16b, the passing hole 14a allowing the projectile 16a to be projected out from the projecting opening 16b to pass therethrough, and covers or encloses a space between the projecting opening 16b and the passing hole 14a to produce a sample collecting room 14b.

Figure 2:
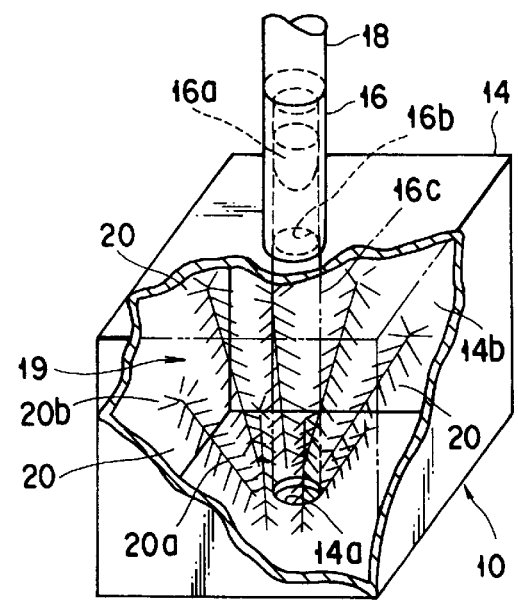
FIG. 2 is an enlarged perspective view schematically showing a main portion of the sample collector of FIG. 1, a part of which is cut away.
Figure 3:
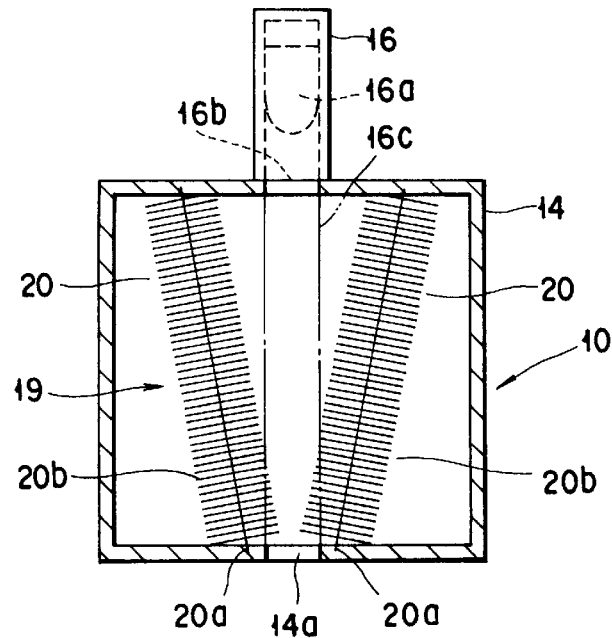
FIG. 3 is an enlarged cross sectional view of the main portion of the sample collector of FIG. 2.

FIGS. 2 and 3 show the enclosed container 14 having a square cubic shape. The enclosed container 14 may have any other cubic shape, such as a rounded or triangular or polygonal cubic shape.

The enclosed container 14 is located near the surface of the celestial body, or preferably in contact with the surface, when the enclosed container approaching and separating means 18 is transformed to its extended condition as shown by the two-dots chain line in FIG. 1. The enclosed container 14 may be provided with a well known precise attitude control unit to bring the projectile passing hole 14a of the enclosed container 14 more closely into contact with the surface of the celestial body. Such precise attitude control unit may be operated by an electric power or a hydraulic power or a pressurized gas power through a remote control. The enclosed container approaching and separating means 18 may be structured to move the enclosed container 14 along the surface of the celestial body toward any position in a certain range.

Further, a peripheral portion of the projectile passing hole 14a in the outer surface of the enclosed container 14 may be structured to have a substantially half sphere shape or a substantially cone shape so that the peripheral portion may be brought into contact with the surface of the celestial body as the object from which the samples to be collected, without producing any gap therebetween.

Kinetic energy absorbing means 19 is arranged around a projectile passing path 16c between the projectile projecting outlet 16b of the projectile projecting unit 16 and the projectile passing hole 14a, in the sample collecting room 14b of the enclosed container 14 to surround the projectile passing path 16c. In this embodiment, the kinetic energy absorbing means 19 is actively structured by a plurality of brushes 20 which are arranged around the projectile passing path 16c to surround it. That is, the brushes 20 function as an active type kinetic energy absorbing means. Each of the brushes 20 has a center rod 20a and numberless bristles 20b planted on the periphery of the center rod 20a. In FIG. 2, in order to clearly show the brushes 20, the brushes 20 are shown not to overlap the bristles 20b of each brush 20 with those of neighbor one and to make a gap therebetween. But the brushes 20 are arranged to actually overlap the bristles 20b of the brushes 20 with those of neighbor ones in all range along each center rod 20a. Each center rod 20a may be fixed at the enclosed container 14 or may be rotatably supported. In FIGS. 2 and 3, a distance between the projectile projecting outlet 16b of the projectile projecting unit 16 and one end or upper end portion of each center rod 20a which is arranged around the projecting opening 16b, is set larger than that between the projectile passing hole 14a of the enclosed container 14 and another end or lower end portion of each center rod 20a which is arranged around the passing hole 14a.

Next, an operation of the sample collector 10 of this embodiment, the structure of which is described above in detail, will be described.

The projectile projecting unit 16 is remote-controlled to project the projectile 16a after the interplanetary space craft lands on the surface of the aimed celestial body and moves the enclosed container 14 by means of the enclosed container approaching and separating means 18 to approach the projectile passing hole 14a to the surface of the celestial body, preferably to bring the passing hole 14a into contact with the surface of the celestial body. The projectile 16a strikes against the surface of the celestial body and forms fragments (samples in this embodiment) of the surface. The fragments are jumped up from the surface. If the surface of the celestial body is relatively soft, materials (also samples in this embodiment) located under and near to the surface are also jumped up from the surface. Almost all of the jumped-up fragments and materials enter into the sample collecting room 14b of the sample collector 14 through the projectile passing hole 14a, and strike against the kinetic energy absorbing means 19 so that the jumped-up fragments and materials the kinetic energy of which is absorbed by the kinetic energy absorbing means 19 are surely collected in the sample collecting room 14b of the enclosed container 14. Even if the jumped-up fragments and materials the kinetic energy of which is absorbed by the kinetic energy absorbing means 19 strike against an inner surface of the sample collecting room 14b, the jumped-up fragments and materials will not damage the inner surface of the sample collecting room 14b. Reaction force generated by the strike of each jumped-up fragment or material is not so large that each jumped-up fragment or material is returned through the kinetic energy absorbing means 19 to exit out from the projectile passing hole 14a of the enclosed container 14 to the outer space thereof.

If the projectile 16a rebounds from the surface of the celestial body and enters into the enclosed container 14, the rebounded projectile 16a strikes the kinetic energy absorbing means 19 and is collected in the sample collecting room 14b of the enclosed container 14 after the kinetic energy thereof is absorbed by the absorbing means 19. Thus, the rebounded projectile 16a will not damage the inner surface of the sample collecting room 14b when it strikes against the inner surface.

The sample collector 10 may be further provided with a shield member 22 like a brim, as shown by a two-dots chain line in FIG. 1. Even if the fragments of the surface of the celestial body formed and jumped up by the strike of the projectile 16a against the surface, and the materials located under and near the surface and formed and jumped up by the strike escape out from a gap between the projectile passing hole 14a of the enclosed container 14 and the surface of the celestial body, the shield member 22 surely prevents the fragments and the materials from striking the sample collector 10 and the interplanetary spacecraft 12 and damaging them. As shown by a two-dots chain line in FIG. 1, the shield member 22 is preferably attached on an outer surface of the enclosed container 14 at a position located between the projectile passing hole 14a and a half level of the height of the enclosed container 14, so that the shield member 22 does not prevent the enclosed container 14 from moving to approach its projectile passing hole 14a to the surface covering of the celestial body, preferably to make the passing hole 14a in contact with the surface, and surely prevents the fragments and the materials escaped out from the gap between the projectile passing hole 14a of the enclosed container 14 and the surface of the celestial body from moving upward toward the sample collector 10 and the interplanetary spacecraft 12. An extending length of the shield member 22 may be substantially the same as the height of the enclosed container 14. The shield member 22 may have a plain plate shape as show by two-dots chain line in FIG. 1, or may have a substantially half-sphere shape or a substantially cone shape. More further, the shield member 22 may be a solid type or an extendible and contractible type or a foldable type.

According to the aspect of this invention, the approaching and separating means 18 may be deleted. In this case, the enclosed container 14 may be directly attached to the housing or landing gear 12a of the spacecraft 12 or may be indirectly attached thereto by a simple supporting member which can not approach and separate the container against the object but can be provided with a damper or compliance member, and the projectile passing hole 14a is located adjacently to the object.

Figure 4:
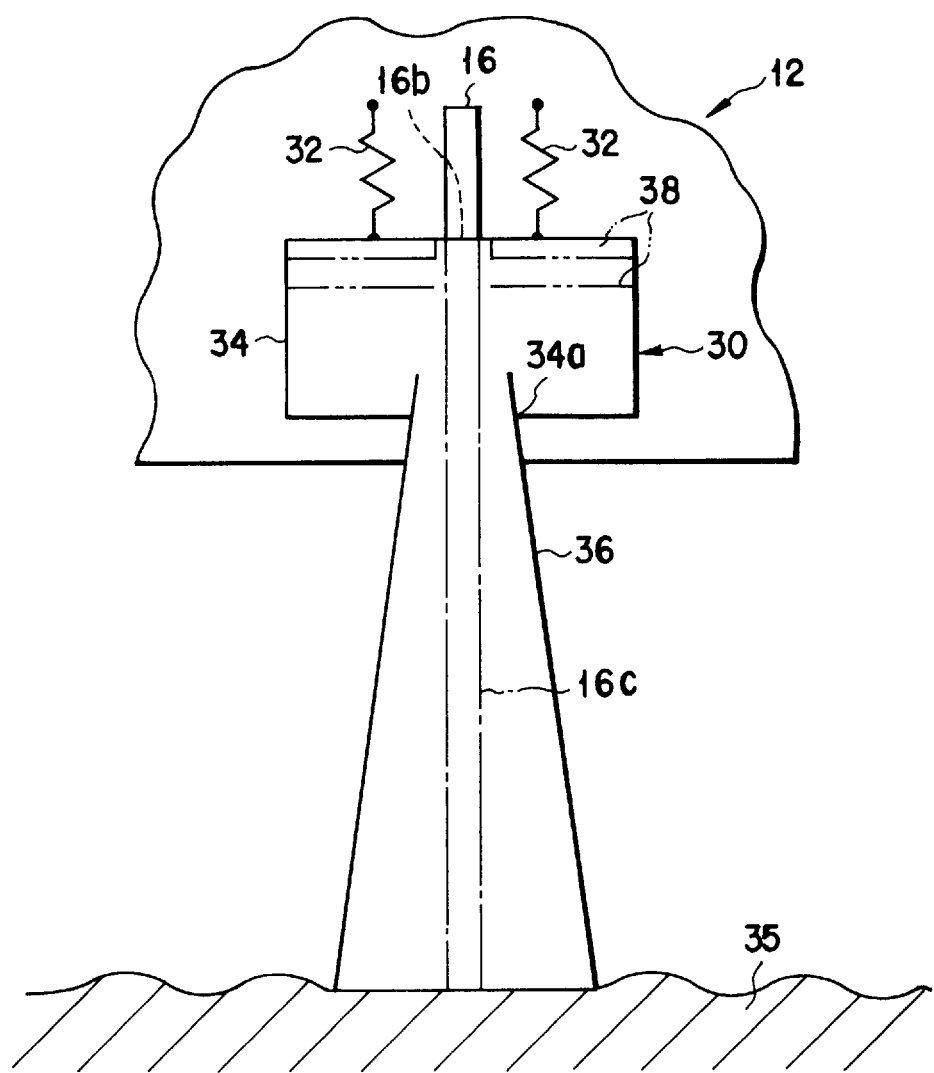
FIG. 4 is a schematical cross sectional view of a main portion of a sample collector according to another embodiment of the present invention.

FIG. 4 shows a schematical cross sectional view of a main portion of a sample collector according to another embodiment of the present invention.

A sample collector 30 of this second embodiment is attached to a supporting base at a position of a housing of the interplanetary spacecraft 12, the position being located above the lower end of the landing gear 12a (see FIG. 1) of the spacecraft 12.

The sample collector 30 may be attached to a supporting base at a position of the landing gear 12a, the position being located above the lower end thereof.

In this embodiment, the sample collector 30 may be attached to the housing with a damper or compliance mechanism 32 interposed therebetween. The sample collector 30 is generally structured by an enclosed container 34 for collecting fragments (that is, samples) of a surface of a celestial body 35 as an object from which samples are to be collected, the projectile projection unit 16 having the same structure as that used in the embodiment shown in FIGS. 1 to 3 and connected to the enclosed container 34.

In this embodiment, the enclosed container 34 includes a sample guide member 36 as a part of the enclosed container 34. The guide member 36 extends from a projectile passing hole 34a of the container along the projectile passing path 16c toward outside of the container to surround the projectile passing path 16c.

When the spacecraft 12 is landed on the surface of the celestial body 35, the extending end of the sample guide member 36 contacts the surface of the celestial body 35 tightly, as shown in FIG. 4. At this time, since the sample collector 30 is attached to the housing of the spacecraft 12 by means of the damper or compliance mechanism 32, the sample guide member 36 is not damaged by the striking of it against the surface of the celestial body 35 and can contact closely the surface of the celestial body 35.

Further, in this embodiment, the enclosed container 34 including the sample guide member 36 serves as a passive type kinetic energy absorbing means which is arranged around the projectile path 16c between the projection outlet 16b of the projectile projecting unit 16 and the projectile passing hole 34a of the enclosed container 34.

In this embodiment, since the extending end of the sample guide member 36 serves as an entrance of the projectile passing hole 34a, fragments (samples in this embodiment) of the surface of the celestial body 35 formed by striking of the projectile (see FIGS. 2 and 3) against the surface is introduced into the sample collecting room in the enclosed-container 34 through the projectile passing hole 34a by the guide member 36. The fragments collide with the inner surface of the guide member 36 many times and are absorbed their kinetic energy by the collision until they are introduced into the sample collecting room. Therefore, the fragments can be collected into the sample collecting room in the enclosed container 34 without breaking the container 34 or the housing of the spacecraft 12.

When necessary, on the inner surface of the guide member 36 or in the enclosed container 34 an independent kinetic energy absorbing means 38 such as a shock absorbing material, a brush, a net or a bag may be provided.

Especially, the independent kinetic energy absorbing means 38 may be attached on the inner surface of the enclosed container 34 or may be arranged in the sample collecting room thereof, as shown by two-dot-chain lines in FIG. 4. The arrangement of the independent kinetic energy absorbing means 38 in the collecting room may be free as far as they absorb the kinetic energy of the fragments so as not to return the fragments through the projectile passing hole 34a toward the surface 35. The guide member 36 may have any shape as far as it can not only effectively absorb the kinetic energy of the fragments but also can effectively introduce the fragments into the enclosed body 34.

As is apparent from the above detailed description, the sample collector of this invention can collect a sample or samples with a good sample collecting efficiency even if a projectile fails to stick on a surface of an object from which the sample is to be collected, and can exactly prevent fragments (that is, samples) of the surface of the object which are formed by striking of the projectile against the surface of the object and are ejected therefrom, and the projectile which is projected on the surface of the object but can not be sticked on the surface to be rebounded therefrom, from striking on the sample collector or a supporting base on which the sample collector is attached and from breaking the sample collector or the supporting base, so that the fragments or the projectile does not damage the sample collector or the supporting base.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

We claim:

1. A sample collector to be attached to a supporting base, comprising:

a projectile projecting unit in which a projectile is loaded and which has a projecting outlet for projecting out the projectile loaded therein;

an enclosed container which is communicated with the projecting outlet of the projectile projecting unit, which has a projectile passing hole arranged at a position located away from the projecting outlet and located adjacently to an object from which a sample is to be collected, the passing hole allowing the projectile to pass through it after the projectile is projected out from the projecting outlet, and which covers a space between the projecting outlet of the projectile projecting unit and the projectile passing hole to provide a sample collecting room; and kinetic energy absorbing means which is arranged around a projectile path between the projecting outlet of the projectile projecting unit and the projectile passing hole of the enclosed container.

2. A sample collector according to claim 1, wherein the kinetic energy absorbing means is arranged in the enclosed container to set a distance between the kinetic energy absorbing means and the projecting outlet of the projectile projecting unit larger than a distance between the kinetic energy absorbing means and the projectile passing hole of the enclosed container.

3. A sample collector according to claim 1, wherein the kinetic energy absorbing means includes a brush.

4. A sample collector according to claim 3, wherein the kinetic energy absorbing means is arranged in the enclosed container and has one end and the other end, the one end being positioned more far away from the projectile passing hole than the other end to set a distance between the one end and the projecting outlet of the projectile projecting unit larger than a distance between the other end and the projectile passing hole of the enclosed container.

5. A sample collector according to claim 1, wherein the supporting base is an interplanetary spacecraft.

6. A sample collector according to claim 1, wherein the sample collector further comprises enclosed container approaching and separating means which connects the supporting base and the enclosed container with each other, and which selectively approaches or separates the projectile passing hole of the enclosed container to or from an object from which the sample is to be collected.

7. A sample collector according to claim 6, wherein the enclosed container approaching and separating means has a rigid structure.

8. A sample collector according to claim 1, wherein the enclosed container includes a sample guide member which extends from the projectile passing hole of the enclosed container to make the extending end of the sample guide member contact an object from which the sample is to be collected, the sample guide member enclosing a projectile path between the projectile passing hole of the container and the object, and guiding the sample separated from the object when the projectile collides against the object, toward the projectile passing hole of the container.

9. A sample collector according to claim 8, wherein the kinetic energy absorbing means is structured by the container to provide multiple collision of the sample with the guide member.

10. A sample collector according to claim 8, wherein the kinetic energy absorbing means is independent of the container and is provided with the container.

11. A sample collector according to claim 10, wherein the kinetic energy absorbing means includes a brush.

* * * * *